(12) United States Patent
Wade

(10) Patent No.: US 11,318,221 B1
(45) Date of Patent: May 3, 2022

(54) WEARABLE AIR CLEANER WITH ULTRAVIOLET LIGHT DISINFECTION

(71) Applicant: James Joseph Wade, Liberty Lake, WA (US)

(72) Inventor: James Joseph Wade, Liberty Lake, WA (US)

(*) Notice: Subject to any disclaimer, the term of this patent is extended or adjusted under 35 U.S.C. 154(b) by 0 days.

(21) Appl. No.: 17/159,099

(22) Filed: Jan. 26, 2021

(51) Int. Cl.
*A61L 9/20* (2006.01)
*A42B 1/012* (2021.01)
*A41D 13/11* (2006.01)

(52) U.S. Cl.
CPC ............ *A61L 9/20* (2013.01); *A41D 13/1184* (2013.01); *A42B 1/012* (2021.01); *A61L 2209/12* (2013.01); *A61L 2209/14* (2013.01)

(58) Field of Classification Search
None
See application file for complete search history.

(56) References Cited

U.S. PATENT DOCUMENTS

| | | | |
|---|---|---|---|
| 5,682,606 A * | 11/1997 | Pospisil | A41D 13/112/173 |
| 5,758,639 A | 6/1998 | Ikonen | |
| 6,023,784 A * | 2/2000 | Yeal | A42B 1/01842/9 |
| 6,154,881 A * | 12/2000 | Lee | A61F 9/0452/9 |
| 6,250,299 B1 | 6/2001 | Danisch | |
| 7,658,891 B1 * | 2/2010 | Barnes | C01B 13/10 422/186.03 |
| 8,757,151 B2 | 6/2014 | Johnstone | |
| 9,877,532 B2 | 1/2018 | Raiffeisen | |
| 11,065,479 B1 * | 7/2021 | Rafalovich | A62B 7/10 |
| 2009/0004047 A1 * | 1/2009 | Hunter | A62B 11/00 422/4 |
| 2009/0025716 A1 * | 1/2009 | Glazman | A62B 18/003 128/201.25 |
| 2010/0095439 A1 * | 4/2010 | Nolan | A42B 3/24 2/421 |
| 2015/0375019 A1 * | 12/2015 | VanDerWoude | A62B 18/003 128/200.28 |
| 2021/0290793 A1 * | 9/2021 | Tung | A41D 13/1192 |

FOREIGN PATENT DOCUMENTS

| | | | |
|---|---|---|---|
| CN | 201640592 U | * | 11/2010 |
| JP | 2011140734 A | * | 7/2011 |
| WO | WO-2019013416 A1 | * | 1/2019 |

OTHER PUBLICATIONS

Innokin Filter Fan Cap, Face Shield Hat with Built-In Dual Fans for 3-6 hrs of Cool Air + Free Breathe 2000mAh Recharge via Micro-USB, 5x 3-Ply Filters, Soft Curtain Clear Faceshield, Carbon—Amazon.com (downloaded Jan. 26, 2021).

* cited by examiner

*Primary Examiner* — Andrew Smyth

(57) ABSTRACT

This invention is directed to a wearable air cleaner where an air cleaning device is incorporated into a hat. The air cleaning device includes a fan unit to pull air through the device and an air filter to capture particles in the air. The air cleaning device also includes ultraviolet light to disinfect the air and pushes the filtered and disinfected air in front of the wearer for breathing.

11 Claims, 5 Drawing Sheets

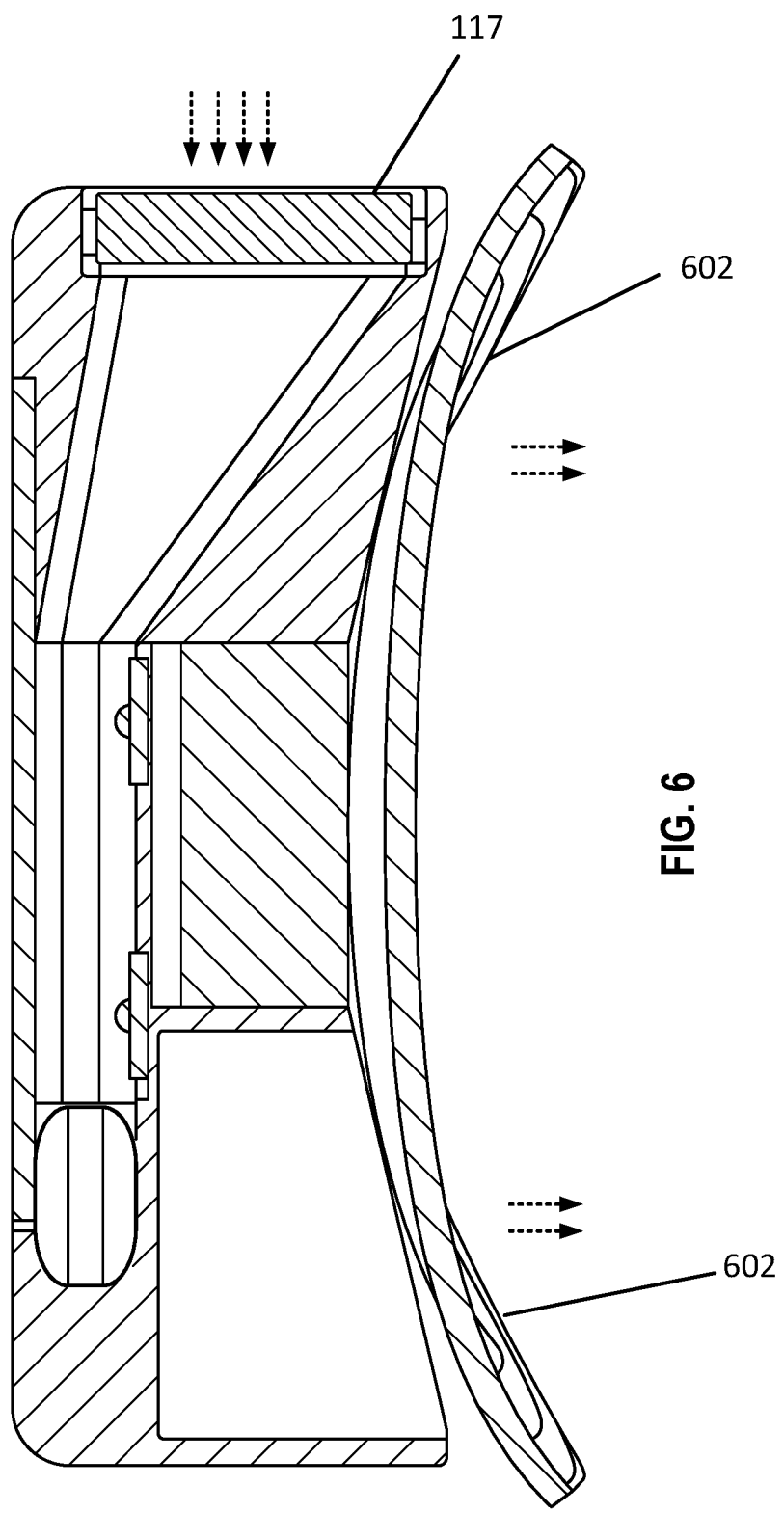

WEARABLE AIR CLEANER WITH ULTRAVIOLET LIGHT DISINFECTION

BACKGROUND

In recent years, there has been many outbreaks of infectious diseases around the World. The need for personal protection against infections has become ever more important. One effective way to protect against infectious diseases, especially those caused by airborne viruses, is by wearing a mask or respirator to lessen the chance of inhaling infectious agents.

A drawback of a mask or respirator is that the filtering mechanism is often not completely effective against all infectious agents, particularly viruses that have a very small cross section. Another drawback is that a mask or respirator with a filter that has meaningful effectiveness against small infectious agents often restricts airflow to such an extent that breathing by the wearer becomes difficult. Yet another drawback is that many people find wearing a mask to be uncomfortable and unrealistic for certain situations, such as when eating, drinking, talking, etc.

There is a need for a better way of personal protection against infectious diseases that balances effective protection and livability.

SUMMARY

This invention is directed to a wearable air cleaner where an air cleaning device is incorporated into a hat. The air cleaning device includes a fan unit to pull air through the device and an air filter to capture particles in the air. The air cleaning device also includes ultraviolet (UV) light to disinfect the air and pushes the filtered and disinfected air in front of the wearer for breathing. The use of UV light enables the air cleaning device to disinfect the air of small infectious agents, such as viruses, without relying solely on the air filter to do so. As a result, a coarser air filter with lower air resistance can be used, thereby enabling a more power efficient fan unit to be used while achieving the desired airflow.

BRIEF DESCRIPTION OF THE DRAWINGS

The drawing figures depict one or more implementations in accord with the present teachings, by way of example only, not by way of limitation. In the figures, like reference numerals refer to the same or similar elements. Furthermore, it should be understood that the drawings are not necessarily to scale.

FIG. 6 shows a front perspective of a cross-sectional view of a wearable air cleaner.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

This invention is directed to a wearable air cleaner for protecting a wearer against infectious agents in the air. The wearable air cleaner employs an air filter as well as UV light to disinfect the air of infectious agents.

Figure 1:
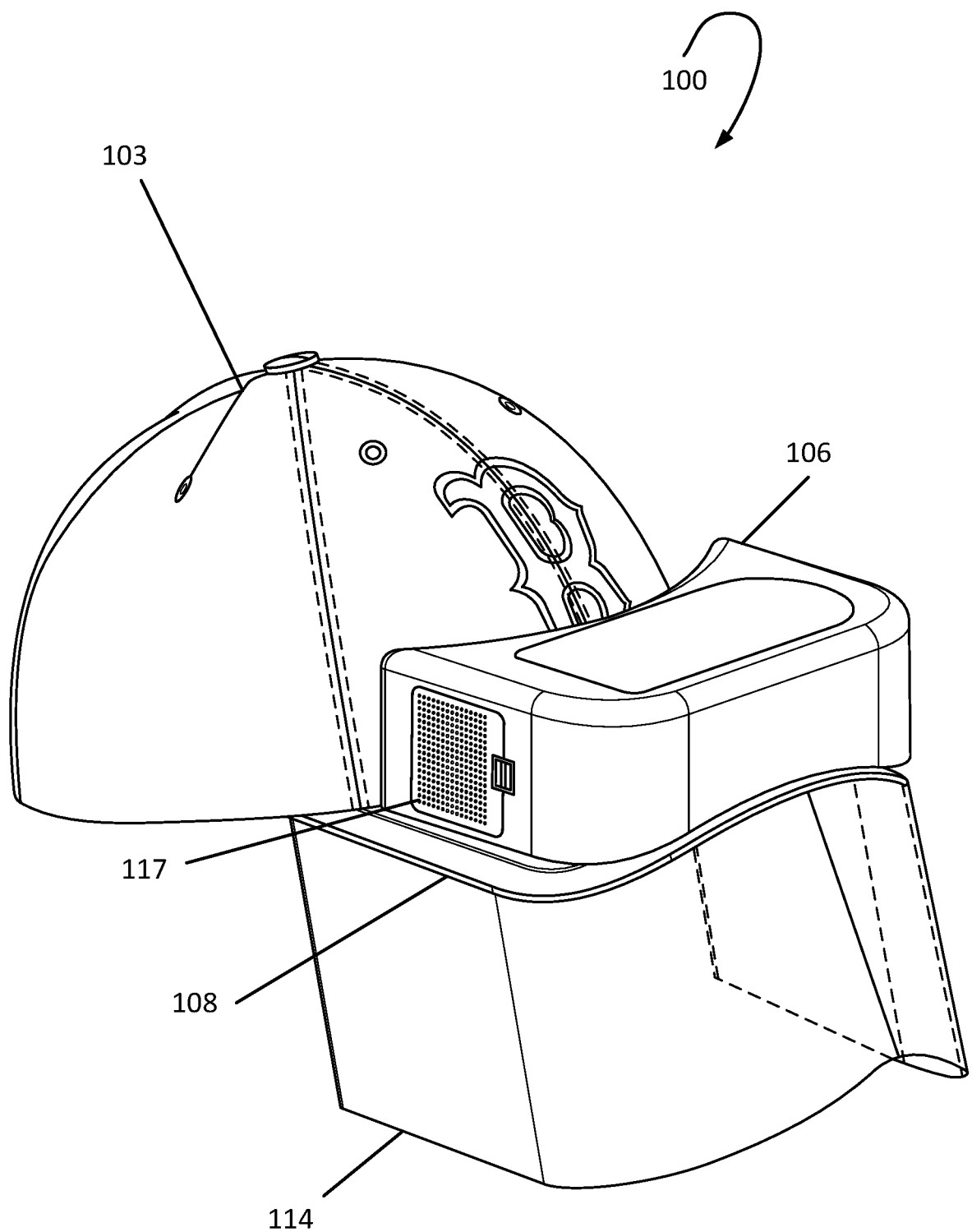
FIG. 1 shows a wearable air cleaner in a perspective view.

FIG. 1 shows one example of such wearable air cleaner as wearable air cleaner 100 in a perspective view. Wearable air cleaner 100 includes hat 103 and air cleaning device 106. FIG. 1 also shows face shield 114 that may optionally be installed on wearable air cleaner 100 for added protection against infectious agents in the air. In one embodiment, face shield 114 is configured with pivot mounts so that face shield 114 can be rotated upward and our of the way of the wearer without having to remove the face shield from wearable air cleaner 100. Air cleaning device 106 is supported by brim 108. Air enters air cleaning device 106 into an air filter through inlet 117.

Figure 2:
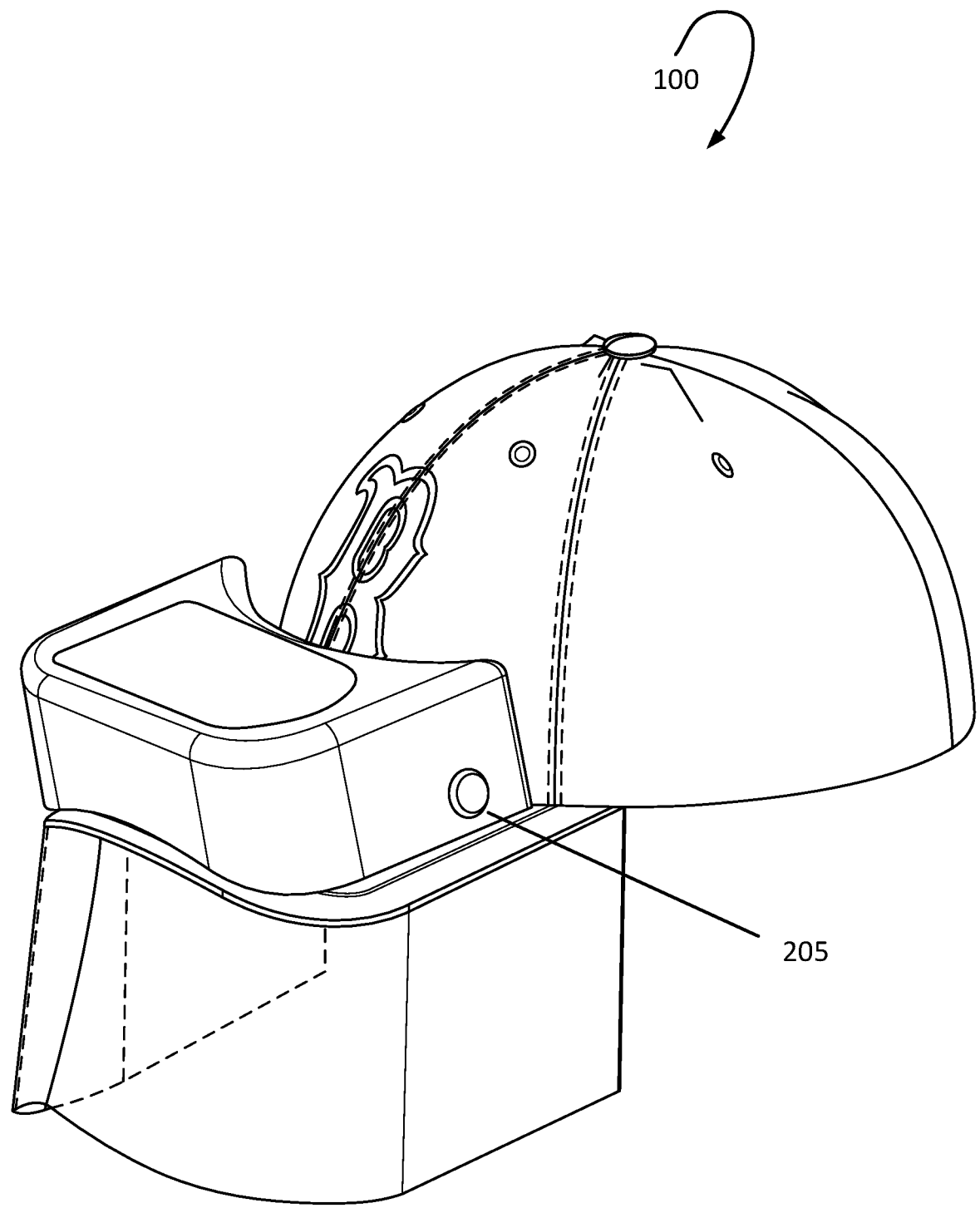
FIG. 2 shows a wearable air cleaner in another perspective view.

FIG. 2 shows wearable air cleaner 100 in another perspective view. Wearable air cleaner 100 includes control button 205 for operating air cleaning device 106. In this example, control button 205 is implemented as a simple, one button unit. Other implementations can be used, such as multiple buttons, toggle switch, slide switch, touch screen, and the like.

Figure 3:
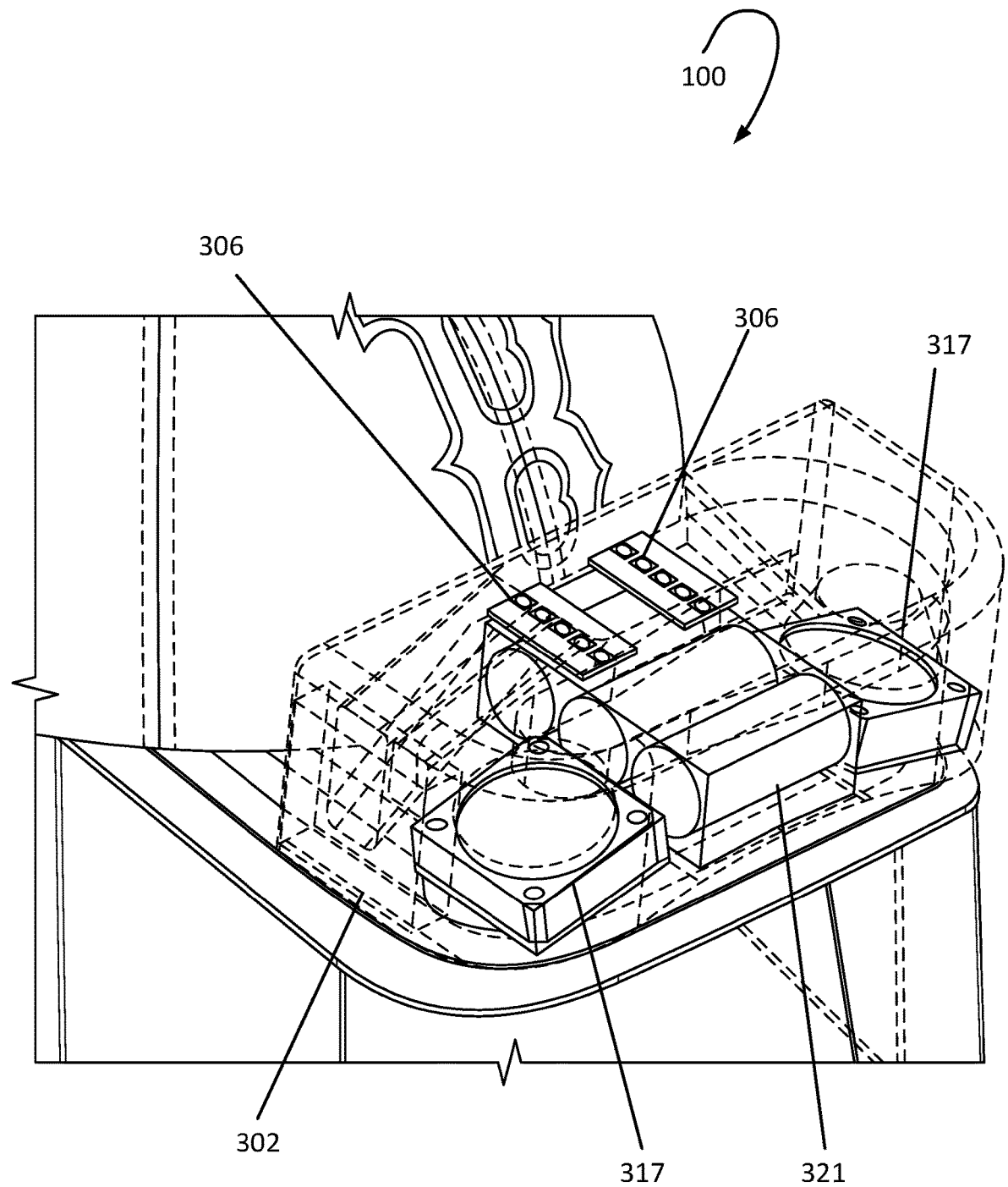
FIG. 3 shows a see-through view of a wearable air cleaner with some example components of a wearable air cleaner.

FIG. 3 shows wearable air cleaner 100 in a see-through view with example components. Wearable air cleaner 100 includes air filter housing 302 that contains an air filter for filtering air entering through inlet 117. Inlet 117 may be implemented as a removable cover for air filter housing 302 to facilitate air filter replacement. The air filter may be a single stage filter or a multi-stage filter.

Many different types of air filter for filtering airborne particles can be used. For example, air filter can be made of fabric, paper, foam and other suitable materials and their combinations. The performance of air filter can be of any suitable rating, such as National Institute of Occupational Safety and Health (NIOSH) efficiency levels, High-Efficiency Particulate Air (HEPA) classes, Minimum Efficiency Reporting Value (MERV) ratings, and the like. For example, the air filter may have a N95 NIOSH rating.

Wearable air cleaner 100 also includes fan unit 317 for pulling air into inlet 117, through air cleaning device 106 and discharging the air through openings in brim 108 in front of the wearer of wearable air cleaner 100. Air cleaning device 106 includes Light Emitting Diode (LED) lights 306 that emit UV light to disinfect air passing through air cleaning device 106. In the preferred embodiment, LED lights 306 emit UV light with wavelength between 100-280 nm (UV-C light), which is particularly effective for killing infectious particles such as viruses.

Air cleaning device 106 includes power unit 321 to power fan unit 317 and LED lights 306. Air cleaning device 106 also includes a controller that electrically connects to fan unit 317 and LED lights 306. The controller can power on fan unit 317 and LED lights 306 individually or both at once by electrically connecting them to power unit 321. The controller can also regulate the speed of fan unit 317 and the light intensity of LED lights 306 by varying the electricity going to fan unit 317 and LED lights 306.

In one embodiment, the controller receives input from control button 205 when it is pushed. For example, the controller may power on both fan unit 317 and LED lights 306 at the same time. The controller may also power on fan unit 317 and LED lights 306 alternatively with successive pushing of control button 205. The controller may vary the speed of fan unit 317 and the light intensity of LED lights 306 with successive pushing of control button 205. Other embodiments include alternative ways for controller to receive input, such as through a remote control, wireless controlling mechanism such as through Bluetooth by another device like a wireless phone, and the like.

Figure 4:
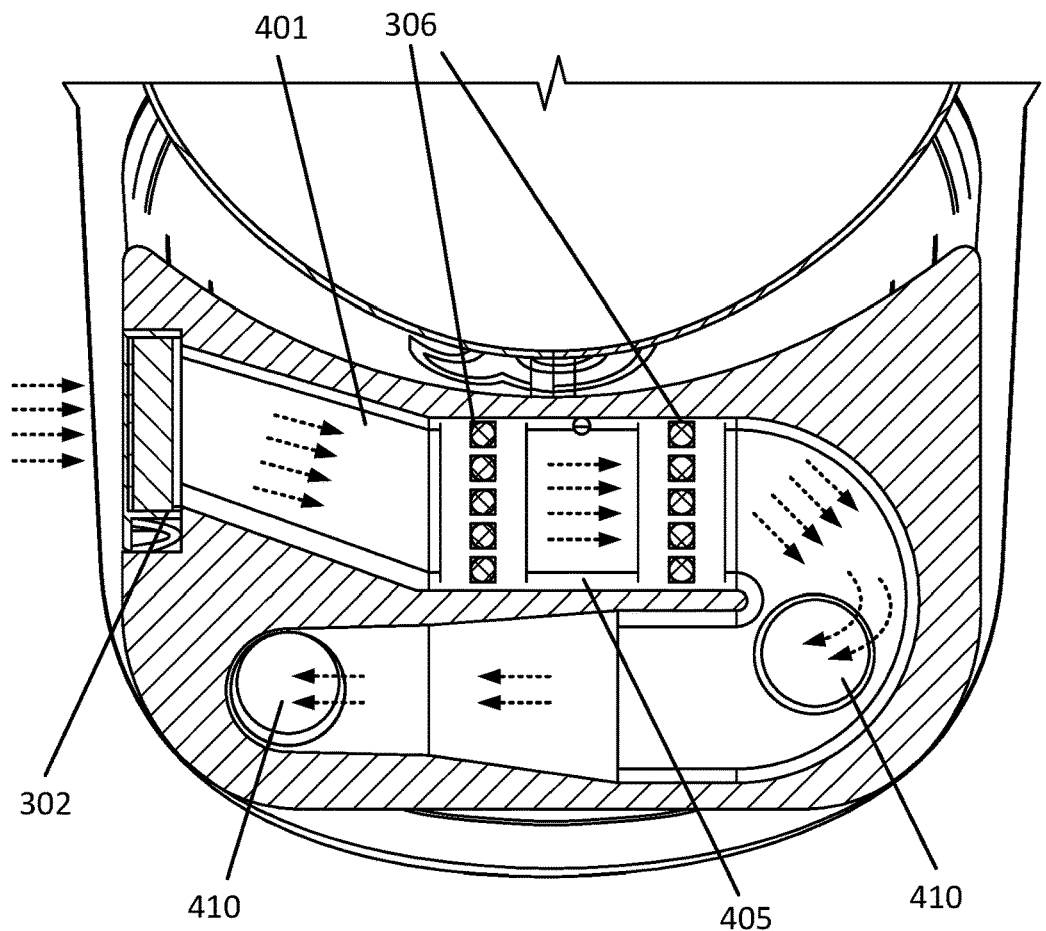
FIG. 4 shows a top perspective of a cross-sectional view of a wearable air cleaner.

FIG. 4 shows a top perspective of a cross-sectional view of wearable air cleaner 100. The cross-sectional view shows the air passageway where air is pulled through air cleaning device 106 by fan unit 317. As shown in the figure, air entered through inlet 117 and the air filter in air filter housing 302 into passageway 401. The filtered air then entered chamber 405 that includes LED lights 306 where the air is disinfected by UV light. After passing through chamber 405, the filtered and disinfected air then are drawn into entrance 410 of fan unit 317 and are pushed into a space under brim 108. In one embodiment, volumetric air flow produced by the fan unit 317 is in a range of 10 cubic centimeter per second and 1000 cubic centimeter per second.

Figure 5:
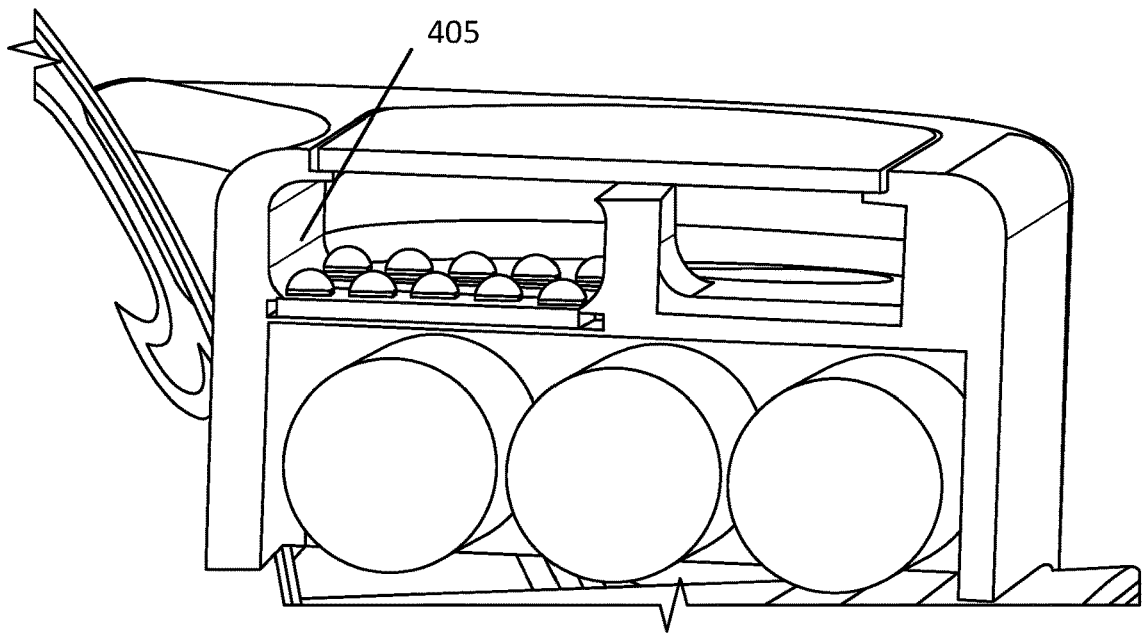
FIG. 5 shows a side perspective of a cross-sectional view of some example components of a wearable air cleaner.

FIG. 5 shows a side perspective of a cross-sectional view of air cleaning device 106. In one embodiment, the height of chamber 405 is within a range of 0.1 centimeter to 10 centimeter. This range would enable the air passing through chamber 405 to be close enough to LED lights 306 to be exposed to sufficient intensity of UV light for disinfection purposes. In another embodiment, the ratio of width of chamber 405 to height is within a range of 0.1 and 10. In yet another embodiment, the dimension of air cleaning device 106 is configured to balance having sufficient air flow to offer protection to the wearer with having a flow speed that is slow enough to allow the air moving through chamber 405 to be disinfected by UV light. In still another embodiment, chamber 405 is lined with light-reflective materials, which can reflect the UV light within the chamber in multiple directions and multiple times to allow the UV light to reach the air in every part of chamber 405 and with more intensity.

FIG. 6 shows a front perspective of a cross-sectional view of wearable air cleaner 106. After passing air cleaning device 100, the filtered and disinfected air are pushed into a space under brim 108. This space is typically where the wearer's face is located. The pushed air creates a region of positive air pressure filled with air that is filtered and disinfected by air cleaning device 106. The positive air pressure region protects the wearer by preventing surrounding air from being breathed in by the wearer. Wearable air cleaner 100 may include face shield 114 to further reinforced the positive air pressure region.

One aspect of the wearable air cleaner as described above is the use of both an air filter and UV light to provide clean air to the wearer. An advantage of this wearable air cleaner is that the use of UV light enables the air cleaning device to disinfect the air of small infectious agents, such as viruses, without relying solely on the air filter to do so. As a result, a coarser air filter with lower air resistance can be used, whereby enabling a more power efficient fan unit to be used while achieving the desired airflow. A more power efficient fan unit is advantageous for many reasons, such as lighter weight, the ability to use a smaller battery, longer running time with a given power source, more air flow with given fan capacity, and the like. For example, in order to effectively disinfect the air of viruses, such as COVID-19 virus, a filter of sufficient filtration effectiveness down to 0.1 microns would need to be used. This would require high filter effectiveness standards, such as NIOSH N99 and MERV 18. Such filters are expensive and very restrictive on airflow. With the wearable air cleaner described above, a filter of less filtration effectiveness can be used to filter particles up to bacterial size. The UV light of the wearable air cleaner would disinfect the viruses that passes through the filter, resulting in air disinfection result comparable or exceeding that of using a filter with significantly higher effectiveness.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claims require more features than are expressly recited in each claim. Rather, as the following claims reflect, inventive subject matter lies in less than all features of a single disclosed example. Thus, the following claims are hereby incorporated into the Detailed Description, with each claim standing on its own as a separately claimed subject matter.

What is claimed is:

1. A wearable air cleaner comprising:
a hat with a brim having an opening;
a face shield rotatable upward about the wearable air cleaner; and
an air cleaning device comprising:
a structural housing for accepting a replaceable air filter, the structural housing including a removable cover for replacing the replaceable air filter;
a chamber with a plurality of LED lights that illuminate the chamber with UV-C light;
a fan unit position over the opening that draws air through the air filter and the chamber;
a power unit;
a controller electrically connecting to the LED lights, the fan unit and the power unit;
wherein the fan unit is powered on in response to being electrically connected to a battery by the controller and pulls air into the air cleaning device and out through the opening;
wherein the air pulled into the chamber is disinfected by the UV-C light emitted by the LED lights at a close distance that are powered on by the controller by being electrically connected to the power unit;
wherein the filtered and disinfected air is pushed by the fan unit through the opening into a space under the brim to form a positive air pressure region in the space; and
wherein the air cleaning device is entirely positioned on top of and supported by the brim without attachment to remainder of the hat.

2. The wearable air cleaner of claim 1, wherein height of the chamber is within a range of 0.1 centimeter to 10 centimeter.

3. The wearable air cleaner of claim 1, wherein ratio of width of the chamber to height of the chamber is within a range of 0.1 and 10.

4. The wearable air cleaner of claim 1, wherein the chamber is lined with light-reflective materials.

5. The wearable air cleaner of claim 1, wherein air flow speed range in the chamber is in a range of 5 centimeter per second to 1000 centimeter per second.

6. The wearable air cleaner of claim 1, wherein volumetric air flow produced by the fan unit is in a range of 10 cubic centimeter per second and 1000 cubic centimeter per second.

7. The wearable air cleaner of claim 1, wherein inlet of the structural housing is on a side of the air cleaning device.

8. The wearable air cleaner of claim 1, wherein the air filter includes one or more stages.

9. The wearable air cleaner of claim 1, wherein the wearable air cleaner further comprising a face shield.

10. The wearable air cleaner of claim 1, the controller is configured to separately power on the fan unit and the LED lights.

11. A wearable air cleaner comprising:
a hat with a brim;
a face shield rotatable upward about the air cleaning device;
an air cleaning device comprising:
a fan unit positioned on top of and supported by the brim;
means for removably housing an air filter;
means for disinfecting in a chamber with UV-C light;
means for drawing air through the air filter and the chamber with the fan unit;
means for controlling an amount of air through the air cleaning device; and
means for discharging the air into a space to create a positive air pressure region in the space;
wherein the air cleaning device is entirely positioned on top of and supported by the brim without attachment to remainder of the hat.

* * * * *